United States Patent
Smith

(10) Patent No.: US 9,610,164 B2
(45) Date of Patent: Apr. 4, 2017

(54) STIFFENING STRUCTURE IN A PROSTHETIC MEMBER

(71) Applicant: Biomet Manufacturing, LLC, Warsaw, IN (US)

(72) Inventor: Aaron P. Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/171,227

(22) Filed: Feb. 3, 2014

(65) Prior Publication Data

US 2015/0216668 A1 Aug. 6, 2015

(51) Int. Cl.
  *A61F 2/34* (2006.01)
  *A61F 2/30* (2006.01)
  *B22F 3/105* (2006.01)
  *B33Y 80/00* (2015.01)
  *B33Y 10/00* (2015.01)
  *B22F 7/00* (2006.01)
  *B22F 5/00* (2006.01)

(52) U.S. Cl.
  CPC .............. *A61F 2/34* (2013.01); *A61F 2/3094* (2013.01); *B22F 3/1055* (2013.01); *B22F 7/004* (2013.01); *B33Y 10/00* (2014.12); *B33Y 80/00* (2014.12); *A61F 2002/30013* (2013.01); *A61F 2002/3097* (2013.01); *A61F 2002/30769* (2013.01); *A61F 2002/30879* (2013.01); *A61F 2002/30894* (2013.01); *A61F 2002/30962* (2013.01); *A61F 2002/3412* (2013.01); *B22F 2005/005* (2013.01)

(58) Field of Classification Search
  CPC .................... A61F 2/34; A61F 2002/34; A61F 2002/3417; A61F 2002/3419; A61F 2002/3422; A61F 2002/3424; A61F 2002/3425; A61F 2002/343
  USPC ............................................. 623/23.5–23.55
  See application file for complete search history.

(56) References Cited

U.S. PATENT DOCUMENTS

| | | | | |
|---|---|---|---|---|
| 4,666,450 A | * | 5/1987 | Kenna | 623/22.28 |
| 4,778,474 A | * | 10/1988 | Homsy | 623/22.14 |
| 5,480,448 A | * | 1/1996 | Mikhail | 623/22.24 |
| 5,549,691 A | * | 8/1996 | Harwin | 623/22.37 |
| 5,676,704 A | * | 10/1997 | Ries et al. | 623/22.21 |
| 5,734,959 A | * | 3/1998 | Krebs et al. | 419/2 |
| 5,782,929 A | * | 7/1998 | Sederholm | 623/22.34 |
| 5,879,398 A | * | 3/1999 | Swarts et al. | 623/22.21 |
| 5,926,685 A | * | 7/1999 | Krebs et al. | 419/2 |
| 5,981,828 A | * | 11/1999 | Nelson et al. | 623/23.51 |
| 6,312,473 B1 | * | 11/2001 | Oshida | 623/23.55 |
| 6,676,704 B1 | * | 1/2004 | Pope et al. | 623/18.11 |
| 6,805,898 B1 | * | 10/2004 | Wu et al. | 427/2.25 |
| 7,001,672 B2 | | 2/2006 | Justin et al. | |

(Continued)

OTHER PUBLICATIONS

U.S. Appl. No. 13/835,932, filed Mar. 15, 2013, Meridew et al.

(Continued)

*Primary Examiner* — Alvin Stewart
(74) *Attorney, Agent, or Firm* — Schwegman Lundberg & Woessner, P.A.

(57) ABSTRACT

A prosthetic member is formed to include a selected thickness to allow for bone retention. The prosthetic member can include a formed support member that can include a rigidifying structure. The rigidifying structure can be formed substantially simultaneously with a formation of at least one portion of the prosthetic member.

15 Claims, 4 Drawing Sheets

(56) References Cited

U.S. PATENT DOCUMENTS

| | | | |
|---|---|---|---|
| 7,597,715 B2* | 10/2009 | Brown et al. | 623/22.32 |
| 7,632,575 B2 | 12/2009 | Justin et al. | |
| 7,666,522 B2 | 2/2010 | Justin et al. | |
| 7,695,521 B2* | 4/2010 | Ely et al. | 623/22.21 |
| 7,758,653 B2* | 7/2010 | Steinberg | 623/23.5 |
| 7,951,412 B2 | 5/2011 | Justin et al. | |
| 8,066,778 B2* | 11/2011 | Meridew et al. | 623/22.32 |
| 8,133,284 B2* | 3/2012 | Ely et al. | 623/22.11 |
| 8,308,810 B2* | 11/2012 | Meridew | 623/22.19 |
| 8,454,705 B2* | 6/2013 | Pressacco et al. | 623/22.33 |
| 8,457,930 B2 | 6/2013 | Schroeder | |
| 8,486,150 B2 | 7/2013 | White et al. | |
| 8,864,826 B2* | 10/2014 | Pressacco | 623/11.11 |
| 9,017,416 B2* | 4/2015 | McMinn | 623/22.24 |
| 2002/0082741 A1 | 6/2002 | Mazumder et al. | |
| 2004/0098127 A1* | 5/2004 | Charlebois et al. | 623/16.11 |
| 2004/0199260 A1* | 10/2004 | Pope et al. | 623/23.5 |
| 2005/0049716 A1* | 3/2005 | Wagener et al. | 623/23.5 |
| 2005/0202371 A1* | 9/2005 | McGuire | 433/201.1 |
| 2005/0267585 A1* | 12/2005 | Sidebotham | 623/22.28 |
| 2005/0273176 A1* | 12/2005 | Ely et al. | 623/22.32 |
| 2006/0241781 A1* | 10/2006 | Brown et al. | 623/23.43 |
| 2006/0263233 A1* | 11/2006 | Gardinier | 419/11 |
| 2007/0173948 A1* | 7/2007 | Meridew et al. | 623/22.24 |
| 2010/0094430 A1* | 4/2010 | Krumdieck | 623/23.5 |
| 2010/0198353 A1* | 8/2010 | Pope et al. | 623/17.11 |
| 2010/0291401 A1 | 11/2010 | Medina et al. | |
| 2011/0153025 A1* | 6/2011 | McMinn | 623/20.32 |
| 2013/0211533 A1 | 8/2013 | Fonte et al. | |
| 2013/0218288 A1 | 8/2013 | Fonte et al. | |

OTHER PUBLICATIONS

Customer reference—Multidisciplinary team puts its heads together to create first laser-sintered cranial implant, e-Manufacturing Solutions, EOS GmbH Electro Optical Systems, www.customIMD.com, 2 pages (Jan. 2012).

DePuy, Customer reference, Laser sintering speeds prototyping and supports in-house production efforts to DePuy Spine, DePuy Spine, Inc., EOS GmbH Electro Optical Systems, 2 pages (Feb. 2012).

New Patent Remedy in the Medical Device Industry, EOS GmbH Electro Optical Systems, 1 page (Nov. 13, 2006).

What is Arcam, Arcam AB: Additive Mfg., www.arcam.com, 2 pages (2009).

Within Medical Software, Osseointegration by Design, Withinlab, 2 pages (2012).

EBM Process, Electron Beam Melting, 3D CAD model, Arcam, 2 pages (2009).

* cited by examiner

STIFFENING STRUCTURE IN A PROSTHETIC MEMBER

FIELD

The subject disclosure relates to a prosthetic member, and particularly relates to a prosthetic member having a selected geometry and internal structure, and at least a method for making the same.

BACKGROUND

This section provides background information related to the present disclosure which is not necessarily prior art.

A prosthetic member or any appropriate implant can be implanted into a subject, such as a human patient, animal patient, or other appropriate patient. The prosthetic member can have various features for various purposes. For example, a thick prosthetic member can be provided such that a high stiffness and rigidity is achieved by the prosthetic member. In various procedures an implant with a selected high stiffness may be required. A stiff implant may require specific material and/or be formed in a manner that is substantially thick. A thick implant may require a large amount of bone removal. Alternatively, a thinner implant may be used if a high rigidity is not required or an amount of material cannot be removed from a subject to allow for implanting of a thick prosthetic member.

SUMMARY

This section provides a general summary of the disclosure, and is not a comprehensive disclosure of its full scope or all of its features.

A prosthetic member can be formed using various manufacturing techniques. For example, a prosthetic member can be formed with casting, forging, machining, or other appropriate manufacturing techniques. According to various embodiments, a prosthetic member can be formed using an additive manufacturing technique, including laser sintering techniques, including those used by EOS GmbH Electro Optical Systems having a place of business in Krailling, Germany. Additive manufacturing techniques may be used to form finished and nearly finished parts of selected designs. In additive manufacturing techniques, a part being formed, such as a prosthetic member, can be formed by sequentially sintering layers of material to another. Formed parts may include selected prosthetic members including an acetabular shell. The additive manufacturing technique allows for substantial control over different features of a whole prosthetic member, including thickness, geometry, porosity, transition from a porous or non-porous region, and other features.

Accordingly, a prosthetic member can be formed to include various distinct sections and regions including a porous portion, a non-porous portion, transitions between porous and non-porous portions, and other features, including internal and external construct shapes. Thus, a prosthetic member can include a selected geometry and physical characteristics. In various examples, a selected physical characteristic can be maintained in a prosthetic member without changing an external geometry of the prosthetic member. For example, forming a support lattice structure can be used to maintain selected characteristics of the member without altering or selecting an internal geometry of the prosthetic member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
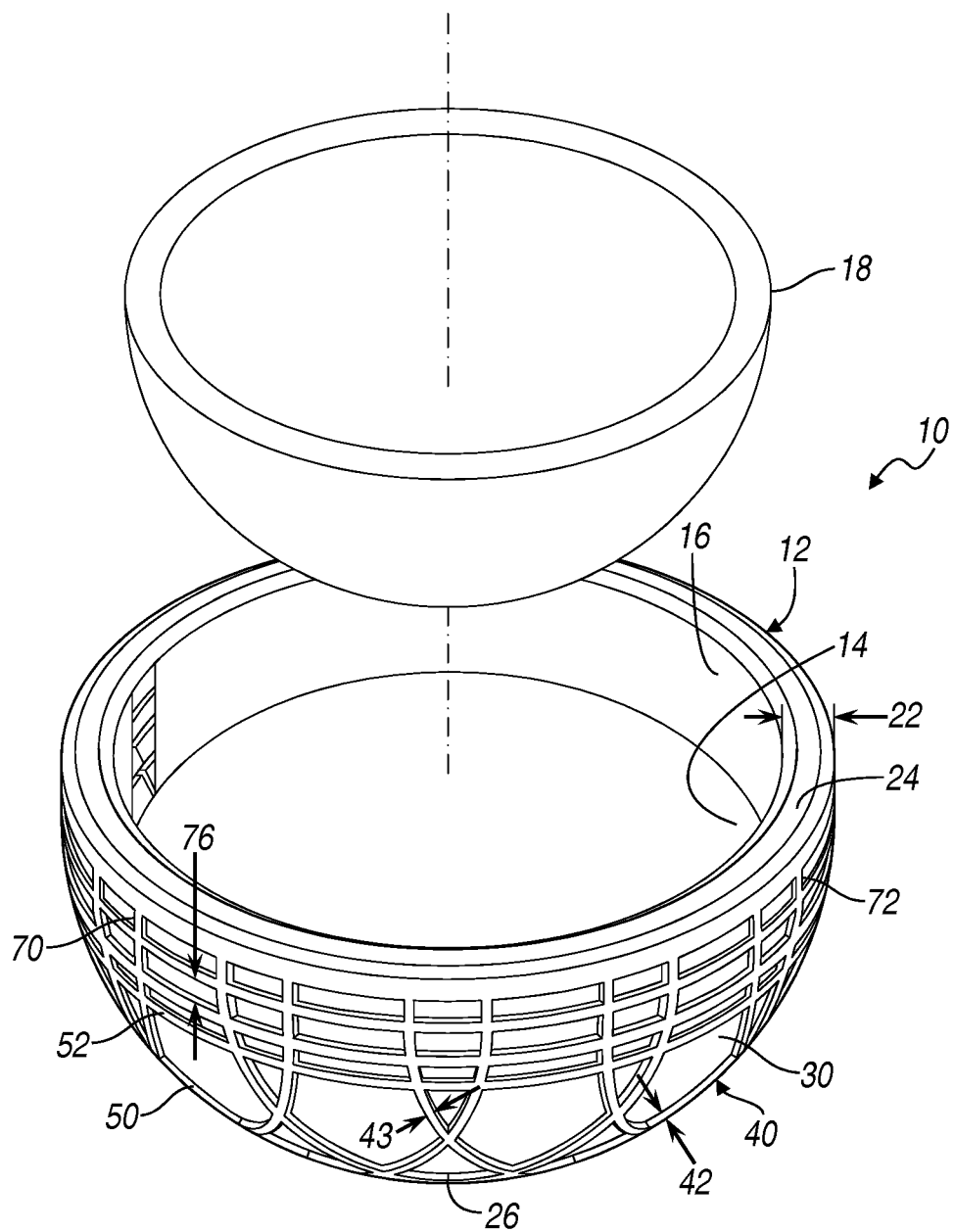
FIG. 1 is a perspective view of a prosthetic member with a support structure, according to various embodiments.

With initial reference to FIG. 1, a prosthetic member 10 may have a first region or portion 12 that may be substantially solid and may be formed using an additive manufacturing technique, such as those used by EOS, discussed above, and also using techniques as disclosed in U.S. patent application Ser. No. 13/835,932, entitled "Directional Porous Coating", incorporated herein by reference. The solid portion 12 may generally define an internal curved area 14 that can define a portion of a sphere and/or be formed as a hemisphere. Additionally, the solid portion 12 may include an upper straight walled portion 16. The straight walled portion 16 may be cylindrical or slanted, as discussed herein.

It is further understood that the interior of the solid portion 12 can be substantially curved throughout and need not include any straight wall or cylindrical portions. Nevertheless, using the various additive manufacturing techniques, the specific geometry of the interior of the solid portion 12 can be formed in any appropriate and selected manner. Further, the interior of the solid portion 12 can be formed to include various features, such as a locking ring, or locking groove (not illustrated), such as that included in the Regenerex® Ring Loc® Modular Acetabular System.

In various embodiments, the solid portion 12 can be designed and/or formed to receive a liner 18. The liner 18 can be a bearing that allows for articulation of a second member, such as a femoral head or a femoral prosthesis. It is understood, however, that the solid portion 12 can be formed of a material and in such a manner to articulate directly with a femoral head or a femoral prosthesis.

Further, the cylindrical portion 16 may define a taper or angle that allows it to lock or securely connect with the liner 18, in an appropriate configuration such as in a taper lock configuration. Accordingly, it is understood that the interior of the solid portion 12 of the prosthesis 10 can be formed to engage or form a locking mechanism, such as a locking ring, or other feature to hold the liner 18 within the solid portion 12.

The solid portion 12 can also have a maximum thickness, such as a thickness 22 of a rim 24 of the solid portion 12. The maximum thickness 22 can be a thickness that is greater than any other thickness of the solid region 12. Moreover, it is understood that the solid region 12 can define any appropriate portion of the prosthesis 10 such as defining an entire portion of the acetabular prosthesis including the rim 24 and extending to an apex or apical region 26.

The solid portion 12 can also define an external curved surface, or under curved surface 30. The curved surface 30 can also define at least a portion of a sphere, such as a hemisphere. The curved under surface 30 can generally have a curve that is the same as the internal curved surface 14. A thickness of the wall between the external curved surface 30 and the internal curved surface 14 can be selected to be an appropriate thickness, such as about 0.1 mm to about 4 mm, including about 0.5 mm to about 3 mm. The thickness may be selected, in part, based upon the material of the solid section, a dimension of a reinforcing rib or lattice structure 40, dimensions of the prosthesis, etc.

Extending from the curved surface 30 can be the reinforcing structure or rib 40. The rib 40 can extend a distance 42 from the surface 30 of the solid section 12. The rib 40 may also include a width 43. The width and distance, it is understood, may be varied over the surface 30 to achieve selected physical characteristics of the prosthesis 10. The rib or lattice 40 can assist in reinforcing or forming a reinforcing structure over the surface 30 of the solid section 12.

In various embodiments, the lattice 40 can vary over the surface 32. For example, the shape of the lattice structure 40 may be varied and can include strips or struts, such as arch portions 50 and ring portions 52. Also, the distance 42 of the lattice portion 40 can vary over various portions of the solid section 12.

Generally, the distance 42, which may be referred to as the depth, of the lattice or rib structure 40 can be about 0.1 mm to about 0.9 mm, including about 0.3 mm to about 0.7 mm, and further including about 0.5 mm. The lattice structure 40 may be formed on the solid portion 12 over the curved portion 30. The thickness from the internal curved surface 14 to the external curved surface can be a selected thickness that can be greater or less than the distance 42 of the rib 40, including a distance of about 0.1 to about 1 cm. As discussed above, the lattice structure 40 can be formed using various manufacturing techniques, such as the additive manufacturing techniques discussed above. Accordingly, the lattice structure 40 can be formed substantially with the solid section 12 in a substantially continuous manner by directing a sintering a selected layer of material to a previous layer to form the solid portion 12, including the surface 30 and the raised or projecting lattice structure 40.

Figure 2:
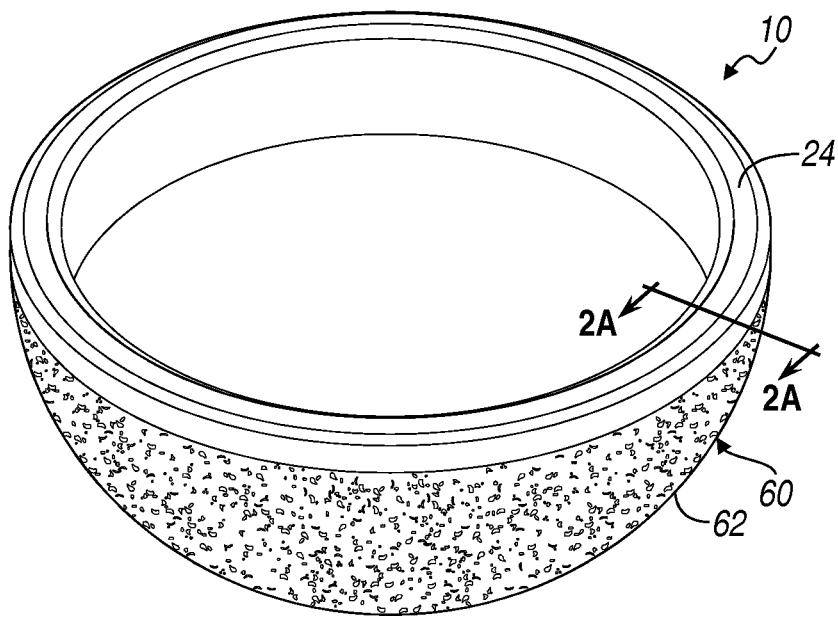
FIG. 2 is a perspective view of a prosthetic member with a first region and a second region, according to various embodiments.

Further, according to various embodiments and with reference to FIG. 2, the prosthesis 10 can include an outer structure or section 60 that can be formed to have a structure different than the solid structure of the section 12. For example, the outer section 60 can be porous. The porosity may assist with various features of the prosthesis 10, such as for bone ingrowth and fixation of the prosthesis 10 to a subject. The porous section 60 can be formed substantially simultaneously with the formation of the solid section 12 using additive manufacturing techniques. The additive manufacturing techniques can form the porous section 60, the solid section 12, and the lattice structure 40 in sequential layers by selecting the connection of the sequential layers.

The porous section 60 can have an average outer surface 62 that may be formed at an average maximum thickness or height from the surface 30. The average height or outer surface of the porous section 60 can generally be substantially congruent with an outer edge 24a of the rim 24. In other words, the rim 24 can form a surface that is substantially continuous with the average outer surface of the porous section 60. That is the outer surface of the porous section 60 need not extend beyond the outer dimension of the rim 24.

Figure 2A:
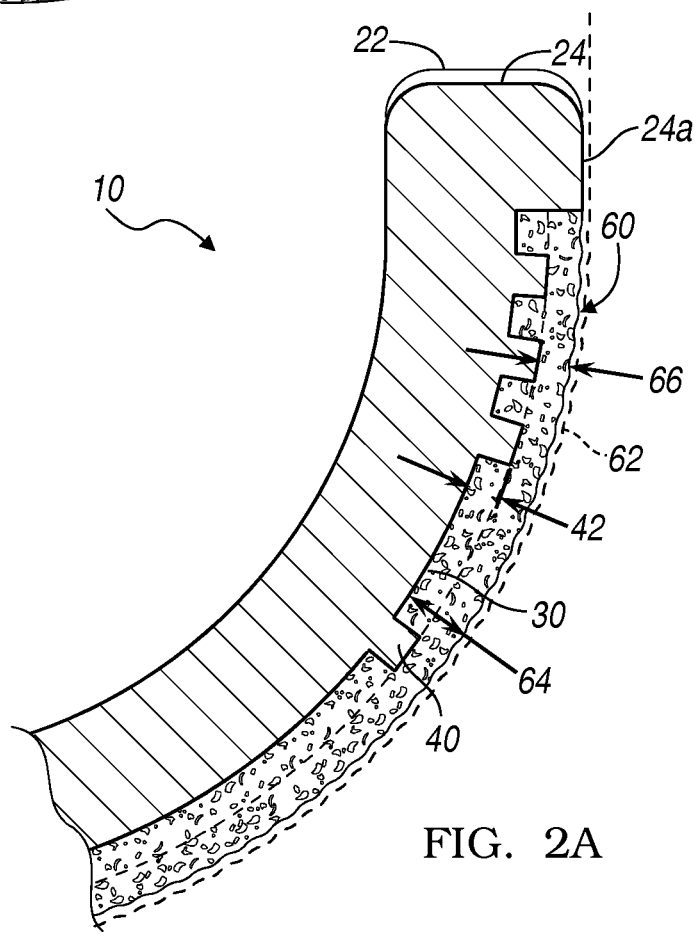
FIG. 2A is a cross-section view of FIG. 2 taken along line 2A.

With reference to FIG. 2A, the porous section 60 that may define or form the outer average surface 62 can have a first dimension 64 that extends from the surface 30 to the outer porous surface 62 that is greater than a distance 66 that extends from a top of the rib 40 to the outer surface 62. However, both of the distances 64 and 66 allow for the porous section 60 to form the outer surface 62 that is substantially continuous from the outer edge 24a of the rim 24. Thus, the porous section 60 can vary in the thickness over the outer surface of the prosthesis 10 depending upon whether the porous section 60 is extending over the lattice portion 40 or only over the surface 30. Thus, the porous portion 60 can be formed with the prosthesis 10 to form a selected geometry, such as a selected external geometry, of the prosthesis 10.

The external surface 62 of the porous section 60 being substantially congruent with the external edge 24a of the rim 24 allows the prosthesis 10 to be formed in a selected size or external geometry for various procedures. For example, the external diameter of the prosthesis 10 can be formed to fit various subjects, such as human patients. For example, an external diameter of about 50 mm, about 60 mm, about 70 mm, and other appropriate diameters of the prosthesis 10 can be formed. Varying the thickness of the porous portion 60 allows it to be formed over the lattice structure 40 without altering an external diameter of the prosthesis 10. The lattice structure 40, therefore, allows for the creation of a selected reinforcement and rigidity of the prosthesis 10. In other words, the porous structure or section 60 being formed at varying thicknesses over the external surface of the solid section 12 allows for the final external diameter of the prosthesis 10 to be substantially continuous and a single selected external diameter.

According to various embodiments, the lattice structure 40 may be formed and designed on the solid section 12 to provide a selected rigidity to the prosthesis 10 without requiring a constant and continuous thickness or selected thickness of the prosthesis 10. For example, the reinforcing lattice 40 can allow for the prosthesis 10 to have the maximum thickness 22 that may be selected less than a thickness that would be required if the prosthesis 10 were formed of a single material and at a single thickness throughout. For example, the maximum thickness 22 can be about 0.5 mm to about 3 cm, further including about 0.5 mm to about 2 cm, and further including about 1.0 mm to about 0.5 cm.

Further, according to various embodiments, the lattice structure 40 can be formed at various and differing patterns based upon a desired rigidity and thickness of the prosthesis 10. For example, as illustrated in FIG. 1, the lattice structure 40 can include the angular rings 52 and the arcs 50 extending from one region near the rim 24 towards the apex 26 and back to the rim 24 at a different region. For example, one of the selected arc portions 50 can extend from a first point 70 near the rim 24 towards the apex 26 and then return towards the rim 24 at a second point 72. Thus, each arc 50 may extend from the first end 70 (at a first point near the rim 24)

to the second end 72 (at a second point near the rim 24), where each of the first points is about 90° apart around the prosthesis 10. It will be understood that an appropriate number of the arcs 50 can be provided, either alone or in combination with an appropriate number of the annular rings 52, to provide a selected rigidity. Further, the annular rings 52 can be formed at selected distances from the rim 24, such as spaced apart by about 0.1 mm to about 2 mm and having a width 76 of about 0.1 mm to about 0.5 mm.

Figure 3:
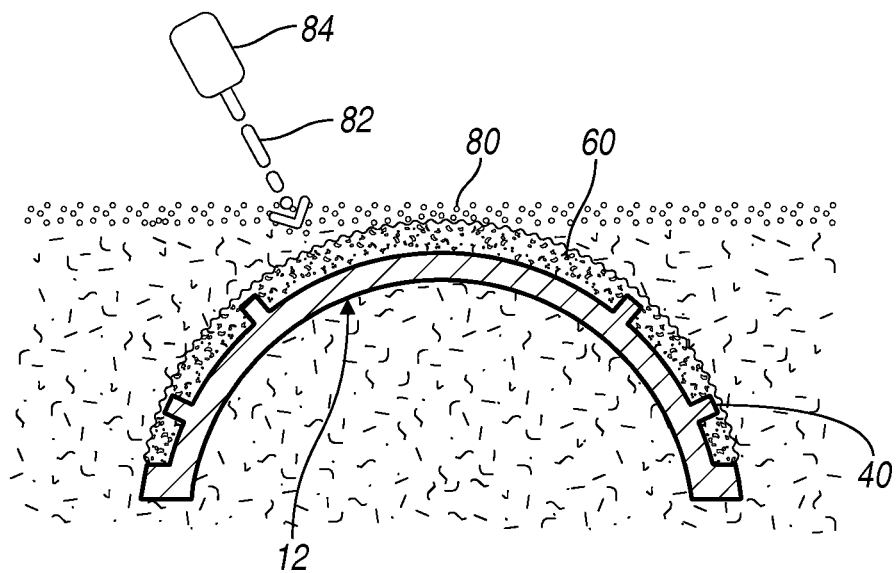
FIG. 3 is a perspective view of a prosthetic member with a support structure, according to various embodiments.

According to various embodiments, the prosthesis 10 may be formed using additive manufacturing techniques and processes, as discussed above. Although additive manufacturing techniques are generally known, a brief description is provided here for clarity. With reference to FIG. 3, according to various embodiments, a layer 80 of a selected material may be placed on a work surface. The selected material may include metal materials. A connection process, such as the addition of adhesives, laser sintering, etc. is used to affix a selected portion of the layer 80 to the previously formed portion of the prosthesis 10 or to begin to form the prosthesis 10. As illustrated in FIG. 3, the layer is laser sintered with a laser beam 82 emitted from the selected laser 84 to a previously formed portion of the solid section 12 and/or the porous section 60. Also, the lattice structure 40 is formed in the same manner and with the selected portion of the layer 80. Thus, it is understood, that all portions of the prosthesis 10 may be formed together with a selected additive manufacturing technique.

Figure 4:
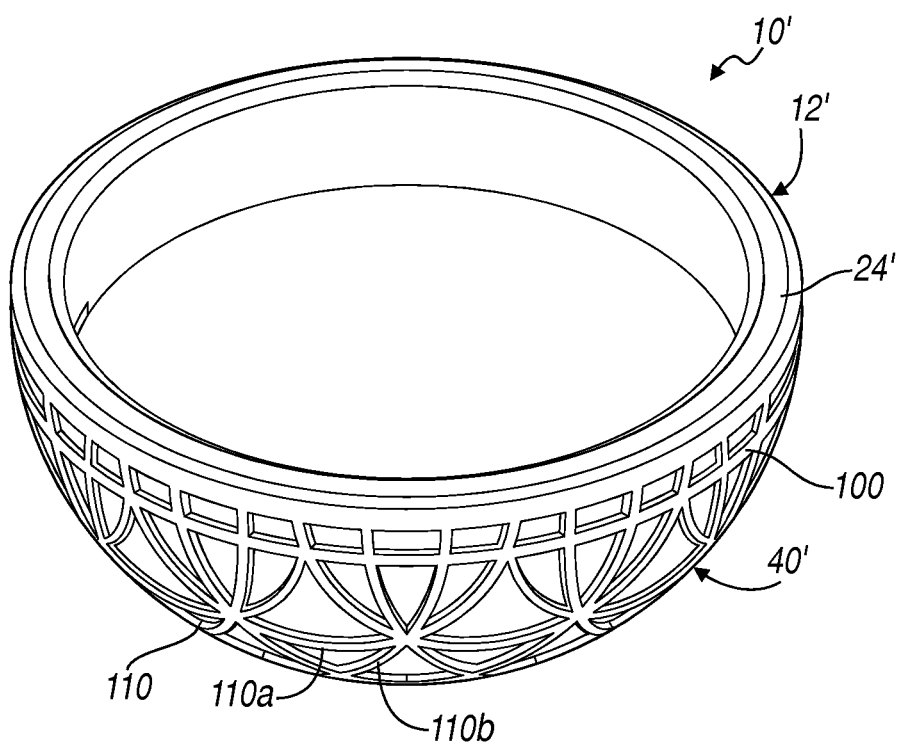
FIG. 4 is a schematic view of a process of forming a prosthetic member, according to various embodiments.
Figure 5:
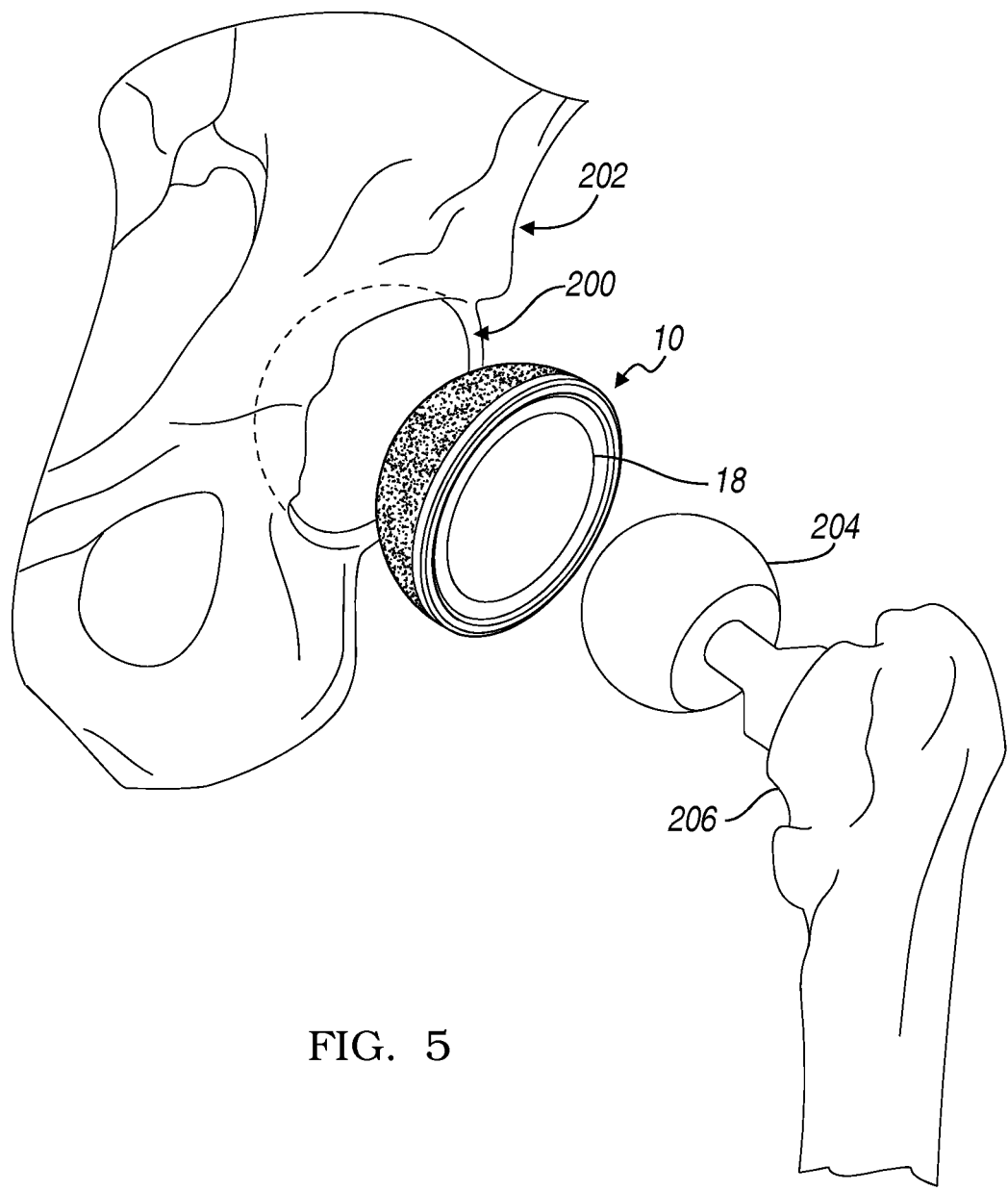
FIG. 5 is a schematic environmental view of a process of positioning a prosthesis member.

With reference to FIG. 4, a lattice structure 40' is illustrated, according to various embodiments, formed on a solid section 12' of a prosthesis 10'. The lattice structure 40' can include a single angular ring 100 and a plurality of various diameter arcs 110. For example, a first arc 110*a* can extend a first distance at its apex from the rim 24' and a second arc 110*b* can extend at a second distance at its apex from the rim 24'. Thus, the varying heights of the arcs 110 can also provide a selected rigidity of the prosthesis 10, 10' for implantation into a subject.

According to various embodiments, the prosthesis 10 can be positioned in an acetabulum 200 of a pelvis 202 of a subject, such as a human patient. The acetabular prosthesis 10 can include the bearing 18 to articulate with a femoral prosthesis head 204 that has been implanted into a femur 206. One skilled in the art will understand preparation of the femur 206 for implantation of the femoral prosthesis 204. Appropriate femoral prostheses can include the Arcos® Modular Femoral Revision Systems sold by Biomet, Inc., having a place of business in Indiana, USA. It is understood, however, that any other appropriate femoral prosthesis can be provided to articulate or connect with the prosthesis 10.

Accordingly, the prosthesis 10 can be formed to engage the acetabulum 200, in an appropriate manner, for articulation with the femoral head 204. The acetabulum 200 can be reamed in an appropriate manner to allow for the retention of a selected amount of bone due to the maximum thickness 22 of the prosthesis 10. The thickness of the prosthesis 10 can be selected, such as minimized, to allow for a large opening within the solid region 12, such as defined by the curved portion 14. The internal curved portion 14 may allow for receipt of the bearing 18 and/or direct articulation with the femoral prosthesis 204. Minimizing the thickness of the prosthesis 10 may allow for a large internal diameter defined by the internal curved region 14. The selected diameter may be selected to be large, such as about 1 centimeter (cm) to about 10 cm, including about 3 cm to about 7 cm. Thus, the acetabular prosthesis 10 can be formed at a thickness to allow for the internal opening to be formed at a selected diameter for articulation of the femoral head while maintaining bone of the pelvis 202 and the acetabulum 200 by forming the thickness 22 of the prosthesis 10 in a selected range.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthesis system, comprising:
    a solid section having an internal surface and a solid external surface;
    a support member formed with and extending from the solid external surface, the support member including at least one sidewall extending from the solid external surface, the support member comprising a plurality of strips forming a lattice;
    a porous section formed with the solid section and on the solid external surface and the support member;
    wherein a porous external surface of the porous section is substantially equal in distance from the internal surface at a first point over the support member and at a second point over the external surface.

2. The prosthesis system of claim 1, further comprising:
    a liner configured to be placed with the solid section.

3. The prosthesis system of claim 1, wherein the solid section and the porous section are formed substantially simultaneously by additive manufacturing.

4. The prosthesis system of claim 1, wherein the solid section and the porous section are formed of a metal material.

5. The prosthesis system of claim 1, wherein the support member includes an annular rib extending around the solid section near a rim.

6. The prosthesis system of claim 1,
    wherein the solid section includes a rim and the solid external surface extends from the rim to an apex;
    wherein the rim extends from the internal surface to a rim external surface,
    wherein the rim external surface extends from the solid external surface.

7. The prosthesis system of claim 6, wherein the porous section includes an external surface that is substantially congruent with the rim external surface.

8. A prosthesis system, comprising:
    a solid section having an internal surface and a solid external surface;

a support member formed with and extending from the solid external surface, wherein the support member includes at least one sidewall extending from the solid external surface;

a porous section formed with the solid section and on the solid external surface and the support member;

wherein a porous external surface of the porous section is substantially equal in distance from the internal surface at a first point over the support member and at a second point over the external surface; and wherein the support member includes an arch that extends from a first point at a rim of the solid section to a second point at the rim and towards an apex of the solid section.

9. The prosthesis system of claim 8, wherein the arch includes a plurality of arches, wherein at least a first arch of the plurality of arches and a second arch of the plurality of arches include different heights measured from the rim.

10. The prosthesis system of claim 8, wherein the support member includes an annular rib extending around the solid section near the rim.

11. A prosthesis system, comprising:

a solid section having a rim portion and a curved portion extending from the rim portion to an apex, wherein the curved portion includes an internal curved surface and an external curved surface, wherein the rim portion has an internal rim surface congruent with the internal curved portion and an external rim surface extending away from the external curved surface;

a support member formed with and extending from the external curved surface, the support member including at least one sidewall extending from the external curved surface and at least one sidewall extending to a support member top surface, the support member comprising a plurality of forming a lattice; and a porous section formed with the solid section and on the external surface and the support member;

wherein a porous external surface of the porous section is substantially congruent with the external rim surface and defines an external dimension of a prosthesis.

12. The prosthesis system of claim 11, wherein the support member top surface is inset from the external rim surface, wherein the porous section overlays the support member.

13. The prosthesis system of claim 12, wherein the support member is formed as at least one elongated portion on the external surface.

14. A prosthesis system, comprising:

a solid section having a rim portion and a curved portion extending from the rim portion to an apex, wherein the curved portion includes an internal curved surface and an external curved surface, wherein the rim portion has an internal rim surface congruent with the internal curved portion and an external rim surface extending away from the external curved surface;

a support member formed with and extending from the external curved surface, wherein the support member includes at least one sidewall extending from the external curved surface and at least one sidewall extends to a support member top surface; and a porous section formed with the solid section and on the external surface and the support member;

wherein a porous external surface of the porous section is substantially congruent with the external rim surface and defines an external dimension of a prosthesis;

wherein the support member top surface is inset from the external rim surface;

wherein the porous section overlays the support member;

wherein the support member is formed as at least one elongated portion on the external surface; and wherein the support member includes an arch that extends over the curved external surface from a first point at the rim portion to a second point at the rim portion and towards the apex.

15. The prosthesis system of claim 14, wherein the support member includes an annular rib extending around the solid section near the rim portion.

* * * * *